United States Patent [19]

Leckrone

[11] Patent Number: 5,713,934
[45] Date of Patent: Feb. 3, 1998

[54] EVOKED AND SPONTANEOUS CARDIAC ACTIVITY DETECTION IN A DUAL-CHAMBER ELECTRONIC PACEMAKER AND METHOD

[75] Inventor: Michael E. Leckrone, Moorpark, Calif.

[73] Assignee: Pacesetter, Inc., Sylmar, Calif.

[21] Appl. No.: 542,088

[22] Filed: Oct. 12, 1995

[51] Int. Cl.$^6$ ..................................................... A61N 1/37
[52] U.S. Cl. ................................................... 607/28
[58] Field of Search ............................ 607/11, 28, 14, 607/9

[56] References Cited

U.S. PATENT DOCUMENTS

| | | | |
|---|---|---|---|
| 4,686,988 | 8/1987 | Sholder | 128/419 |
| 4,809,697 | 3/1989 | Causey et al. | 128/419 |
| 4,815,469 | 3/1989 | Cohen et al. | 128/634 |
| 4,817,605 | 4/1989 | Sholder | 128/419 |
| 4,847,617 | 7/1989 | Silvian | 340/870 |
| 4,940,052 | 7/1990 | Mann et al. | 128/419 |
| 4,940,053 | 7/1990 | Mann et al. | 128/419 |
| 4,969,467 | 11/1990 | Callaghan et al. | 607/28 |
| 5,222,493 | 6/1993 | Sholder | 128/419 |

Primary Examiner—Scott M. Getzow

[57] ABSTRACT

A method of operating a pacemaker and a pacemaker system that cuts short a pacemaker-defined refractory time period whenever capture is not achieved. The pacemaker generates a cardiac stimulation pulse, and in response thereto, initiates an evoked response detection time period and a refractory time period. If an evoked response occurs during the evoked response detection time period, capture is presumed. If an evoked response does not occur during the evoked response detection time period, then capture is not achieved and the refractory time period is terminated, or cut short, thereby lengthening the window during which natural cardiac activity may be sensed. In the event natural cardiac activity is not detected following the termination of the refractory time period, a backup stimulation pulse may be generated.

20 Claims, 6 Drawing Sheets

EVOKED AND SPONTANEOUS CARDIAC ACTIVITY DETECTION IN A DUAL-CHAMBER ELECTRONIC PACEMAKER AND METHOD

FIELD OF THE INVENTION

The present invention relates to implantable pacemakers, and more particularly, to a pacemaker operating in an autocapture mode that prevents a backup (second) stimulation pulse from possibly being issued into, i.e., simultaneously with, a spontaneous or naturally occurring heart contraction following the failure of a first stimulation pulse to achieve capture.

BACKGROUND OF THE INVENTION

An electronic pacemaker is a medical device, typically implanted within a patient, that provides electrical stimulation pulses at a controlled rate to selected chambers of the heart, i.e., the atrium and/or the ventricle. Such stimulation pulses cause the muscle tissue of the heart (myocardial tissue) to depolarize and contract, thereby causing the heart to beat at the controlled rate.

Most pacemakers can be programmed to operate in a demand mode of operation, i.e. to generate and deliver stimulation pulses to the heart only when the heart fails to beat on its own. To this end, the pacemaker senses cardiac activity, i.e., heartbeats, and if the heartbeats do not occur at a prescribed rate, then stimulation pulses are generated by the electronic pacemaker and delivered to an appropriate heart chamber, either the atrium or the ventricle, in order to force the heart to beat.

When operating in a demand mode of operation, the pacemaker defines a period of time, referred to generally as the "escape interval" (which may further be referred to as either an "atrial escape interval" or a "ventricular escape interval," depending upon the mode of operation of the pacemaker) that is slightly longer than the period of time between normal or natural heartbeats. Upon sensing such a "natural," "sinus" or "spontaneous" (non-stimulated or non-paced) heartbeat within the allotted time period, the escape interval is reset, and a new escape interval is started. A stimulation (or pacing) pulse will be generated at the conclusion of this new escape interval unless a natural heartbeat is again sensed during the escape interval. In this way, stimulation pulses are generated "on demand," i.e., only when needed in order to maintain the heart rate at a rate that never drops below the rate set by the escape interval.

The heart rate is monitored by examining the electrical signals that are manifest concurrent with the depolarization or contraction of the myocardial tissue. The contraction of atrial muscle tissue is manifest by the generation of a P-wave, and the contraction of ventricular muscle tissue is manifest by the generation of an R-wave (sometimes referred to as the "QRS complex"). The sequence of electrical signals that represent P-waves, followed by R-waves (or QRS complexes) can be sensed from inside of or directly on the heart by using sensing leads implanted inside or on the heart, e.g., pacemaker leads; or by using external electrodes attached to the skin of the patient. This sequence of electrical signals may be represented graphically as an electrographic representation or electrographic signal, and is typically referred to as the electrogram (EGM) when sensed inside or on the heart, and the electrocardiogram (EKG) when sensed using skin electrodes.

All modern implantable pacemakers are programmable. That is, the basic escape interval (atrial and/or ventricular) of the pacemaker, as well as the sensitivity (threshold level) of the sensing circuits used in the pacemaker to sense P-waves and/or R-waves, as well as numerous other operating parameters of the pacemaker, may be programmably set at the time of implantation or thereafter to best suit the needs of a particular patient. In this way the pacemaker can be programmed to yield a desired performance.

Two periods of time, or intervals, that are commonly programmable within the electronic pacemaker are the atrial refractory period (AREF) and the ventricular refractory period (VREF). The AREF and VREF are initiated in response to an atrial stimulation pulse (A-pulse) or ventricular stimulation pulse (V-pulse). The AREF and VREF are periods of time selected, or programmed, to be equal to or greater than the natural refractory periods of the heart (i.e., those times during which the cardiac tissue is recovering from a prior contraction, either atrial or ventricular, and during which the heart is not capable of contracting again). During AREF, and VREF, any cardiac activity that is sensed by the electronic pacemaker is presumed to be either noise or residual electrical signals resulting from the prior cardiac contraction, and is therefore ignored by the pacemaker logic circuits. The purpose of the AREF or VREF is to prevent the misdetection of spontaneous P-waves or R-waves immediately following the generation of an A-pulse or V-pulse. Any detected cardiac activity during the AREF or VREF should not be used to signal the cardiac pacemaker that an intrinsic or spontaneous P-wave or R-wave has occurred. By making the logic circuitry within the electronic pacemaker ignore cardiac activity sensed during the AREF and the VREF, intrinsic or spontaneous cardiac activity cannot normally be validly sensed until after the electrical effects of the stimulation pulse and its evoked response have dissipated.

The operation of a pacemaker as described above presupposes that a stimulation pulse generated by the pacemaker effectuates capture. As used herein, the term "capture" refers to the ability of a given stimulation pulse generated by a pacemaker to cause depolarization of the myocardium, i.e., to cause the heart muscle to contract, or to cause the heart to "beat." In the case of the ventricular stimulation pulse (V-pulse), capture is manifest by an evoked ventricular response (evoked R-wave). Similarly, in the case of the atrial stimulation pulse (A-pulse), capture is manifest by an evoked atrial response (evoked P-wave). A stimulation pulse that does not capture the heart is thus a stimulation pulse that may just as well have not been generated, for it has not caused the heart to respond, i.e., to beat or contract. Such a non-capturing stimulation pulse not only represents wasted energy—energy drawn from the limited energy resources (battery) of the pacemaker—but worse still, if the logic circuits of the pacemaker presuppose that each stimulation pulse generated by the pacemaker captures the heart, the non-capturing stimulation pulse caused the logic circuits to make a false assumption that the stimulation pulse achieved capture. Thus, if the stimulation pulse does not capture the heart, then the pacemaker logic circuits may be controlling the operation of the pacemaker based on this false assumption, and may thus control the pacemaker in an inappropriate manner. Such inappropriate control of the pacemaker can result in dangerous arrhythmias and the like in the heart. There is thus a critical need for a way of determining whether a given stimulation pulse has effectuated capture.

While there are many factors that influence whether a given stimulation pulse effectuates capture, a principal factor is the energy of the stimulation pulse. The energy of the stimulation pulse, in turn, is determined by the amplitude and pulse width of the atrial or ventricular stimulation pulse generated by the pacemaker. Advantageously, in a programmable pacemaker, both the amplitude and pulse width of the stimulation pulse are typically parameters that may be programmed into the pacemaker or programmably controlled by the pacemaker.

A common technique used to determine if capture has been effectuated is to look for an "evoked response" (ER) immediately following a stimulation pulse. The evoked response is a physical and electrical response of the heart that results from the application of a stimulation pulse to the heart. When capture occurs, the evoked response is manifest in an intracardiac P-wave or R-wave indicating contraction of the respective atrial or ventricular cardiac tissue in response to the applied stimulation pulse. For example, if a stimulation pulse is applied to the ventricle (referred to herein as a ventricular stimulation pulse or V-pulse), any response sensed by the ventricular sensing circuits of the pacemaker immediately following the application of the V-pulse is assumed to be an evoked ventricular response (also referred to as an evoked R-wave) that evidences capture of the ventricles. Similarly, if a stimulation pulse is applied to the atrium (referred to herein as an atrial stimulation pulse or A-pulse), any response sensed by the atrial sensing circuits of the pacemaker immediately following the application of the A-pulse is assumed to be an evoked atrial response (also referred to as an evoked P-wave) that evidences capture of the atria.

In order to detect whether an evoked P-wave or an evoked R-wave occurs immediately following an A-pulse or a V-pulse, respectively, a period of time, referred to as the atrial post-stimulus response detection window or the ventricular post-stimulus response detection window, respectively, is initiated by the pacemaker in response to the generation of an A-pulse or a V-pulse. During the atrial or ventricular post-stimulus response detection window, the logic circuitry within the electronic pacemaker, associated with the atria or ventricles, respectively, becomes sensitive to the evoked P-wave or the evoked R-wave. Any cardiac activity occurring after the atrial post-stimulus response detection window or ventricular post-stimulus response detection window has expired, respectively, is not considered to be an evoked response, but rather is considered to be spontaneous or intrinsic cardiac activity. That is, as used herein, the term "evoked response" refers to P-waves or R-waves that occur during the post-stimulus evoked response detection window. The term "spontaneous or intrinsic response" refers to P-waves or R-waves that occur after the post-stimulus evoked response detection window.

By detecting the evoked P-wave or evoked R-wave, the electronic pacemaker is able to detect whether the cardiac stimulation pulse (A-pulse or V-pulse) was effective in capturing the heart, i.e., causing a contraction in the respective chamber of the heart. In the event no evoked response is detected by the pacemaker during the atrial or ventricular post-stimulus response detection window, and in the event the electronic pacemaker is in an autocapture mode, the pacemaker initiates a backup (second) response, which includes generating a backup (second) stimulation pulse some time after the atrial post-stimulus response detection window or ventricular post-stimulus response detection window expires. The backup stimulation pulse is typically an A-pulse or V-pulse of greater amplitude, pulse width or both than the initial atrial or ventricular stimulation pulse. The backup stimulation pulse is designed to capture the heart when the initial, lower amplitude and/or lower pulse width stimulation pulse was unable to do so.

Problematically, however, there are circumstances wherein the combination of the atrial post-stimulus response detection window and the AREF, or the ventricular post-stimulus response detection window and the VREF, can be detrimental in an electronic pacemaker operating in the autocapture mode. Namely, when, for example, a V-pulse is generated, initiating the ventricular post-stimulus response detection window and the VREF, the logic circuitry is insensitive to sensed cardiac activity for a period of time between the expiration of the ventricular post-stimulus response detection window and the expiration of the VREF. In the event a spontaneous depolarization (R-wave) occurs, or begins to occur, during this period of insensitivity, the spontaneous depolarization (R-wave) will go undetected. This is problematic in cases wherein no evoked R-wave is detected during the ventricular post-stimulus response detection window, and, as a result, the backup response, including generation of a backup V-pulse, is initiated. Unfortunately in this case, the backup V-pulse may be "blindly" generated during the undetected spontaneous R-wave, potentially causing dangerous arrhythmias in the heart. Thus, what is needed is a system and method for determining whether a backup stimulation pulse can be safely delivered to the heart following delivery of an initial stimulation pulse for which capture was not achieved, i.e., for which no evoked response was detected.

SUMMARY OF THE INVENTION

The present invention advantageously addresses the needs above as well as other needs by providing a system and method for detecting whether a cardiac response has been evoked by a pacemaker-generated stimulus (A-pulse or V-pulse), or whether spontaneous cardiac activity (natural P-wave or R-wave) has occurred, before a backup electrical stimulation pulse is permitted to be generated by the electronic pacemaker; and for preventing the generation of the backup stimulation pulse in the event evoked or spontaneous cardiac activity is detected.

In one embodiment, having particular advantages when used in an electronic pacemaker operating in an autocapture mode, the invention can be characterized as a method of preventing the generation of a backup stimulation pulse in the event either evoked cardiac activity or intrinsic (or spontaneous) cardiac activity is detected following the initial stimulation pulse. In this embodiment, an initial cardiac stimulation pulse is generated, and in response thereto an evoked response detection time period, or window, and a refractory time period (longer than the evoked response detection time period) are simultaneously initiated. A determination is next made as to whether an evoked response occurs during the evoked response detection time period. In the event an evoked response is not detected during the evoked response detection time period, the refractory time period is immediately terminated, or cut off, thereby allowing any natural (i.e., intrinsic or spontaneous) cardiac response that occurs thereafter to be detected. Such "cutting off" of the refractory time period results in the ending of the refractory time period at a time before a time at which the refractory time period would otherwise end. If a spontaneous response is detected following the terminating (i.e., "cutting off") of the refractory time period, then the pacemaker continues to operate in its normal manner. Only when a spontaneous response is not detected following the "cutting off" of the refractory time period is a backup (second) cardiac stimulation pulse permitted to be generated. The backup stimulation pulse is never generated when a spontaneous response is detected following the "cutting off" of the refractory time period.

In another embodiment, the invention can be characterized as an implantable electronic pacemaker. The electronic pacemaker employs pulse generator means, first timing means, second timing means, detecting means, and terminating means. In operation, the pulse generator means generates a first cardiac stimulation pulse at an appropriate time in the cardiac pacing cycle. The first timing means initiates an evoked response detection time period in response to the first cardiac stimulation pulse. The second timing means likewise initiates a refractory time period in response to the generation of the first cardiac stimulation pulse. The detecting means detects whether an evoked response occurs during the evoked response detection time period, and the terminating means immediately terminates the refractory time period as soon as the detecting means detects that an evoked response did not occur during the evoked response detection time period. By terminating the refractory time period in this manner, any natural cardiac activity that occurs thereafter (after termination of the refractory time period) can be detected, thereby preserving "correct" information for the continued operation of the pacemaker.

It is thus a feature of the present invention to detect whether a cardiac response has been evoked by a pacemaker-generated stimulus, or whether spontaneous (i.e., not evoked) cardiac activity has occurred.

It is another feature of the invention, in one embodiment, to prevent the generation and issuance of a backup stimulation pulse (used, e.g., in an autocapture mode) in the event evoked cardiac activity is detected before an evoked response detection time period expires or in the event spontaneous cardiac activity is detected after the evoked response detection time period expires.

It is a further feature of the invention, in another embodiment, to prevent the generation of a backup stimulation pulse during a spontaneous cardiac contraction.

It is an additional feature of the invention to immediately terminate a pacemaker-generated refractory time period whenever a determination is made that capture has not been achieved.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description of the presently contemplated best mode of practicing the invention is not to be taken in a limiting sense, but is made merely for the purpose of describing the general principles of the invention. The scope of the invention should be determined with reference to the claims.

Figure 1:
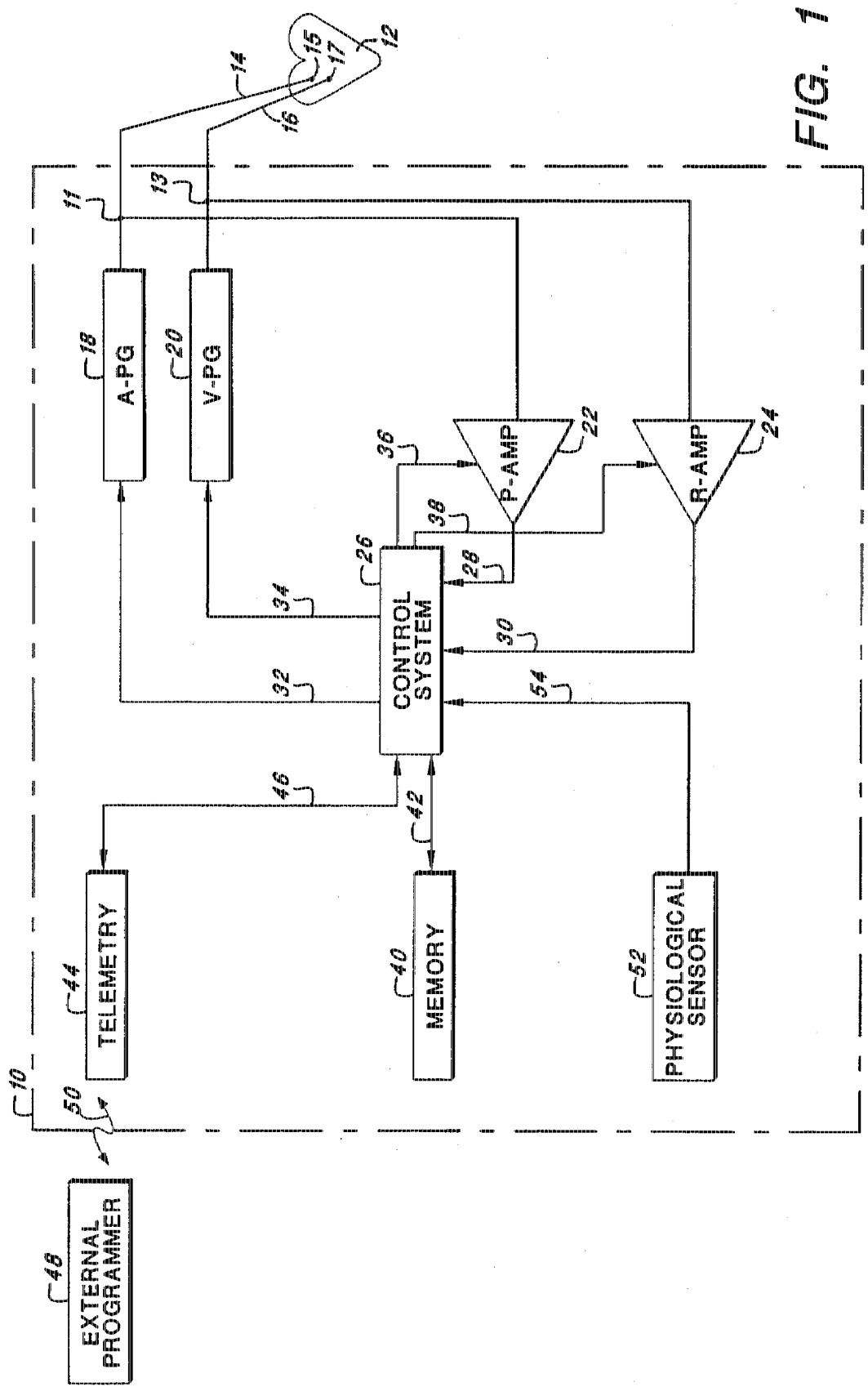
FIG. 1 is a functional block diagram of a dual-chamber implantable electronic pacemaker.

Referring to FIG. 1, a functional block diagram of an exemplary dual-chamber implantable electronic pacemaker 10 is illustrated in accordance with the teachings of one embodiment of the invention. The electronic pacemaker 10 is coupled to a heart 12 by way of leads 14, 16, which are coupled to the pacemaker 10 at respective connection points 11, 13. The lead 14 has an electrode 15 that is in contact with one of the atria of the heart, and the lead 16 has an electrode 17 that is in contact with one of the ventricles of the heart. The leads 14, 16 carry stimulating pulses to the electrodes 15, 17 from either an atrial pulse generator (A-PG) 18 or a ventricular pulse generator (V-PG) 20, respectively, as is known in the art. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular channel sense amplifier (R-AMP) 24, as is also known in the art. The pacemaker 10 is housed in an implantable hermetically sealed housing (not shown), such as are known in the art of implantable electronic pacemakers.

Figure 6:
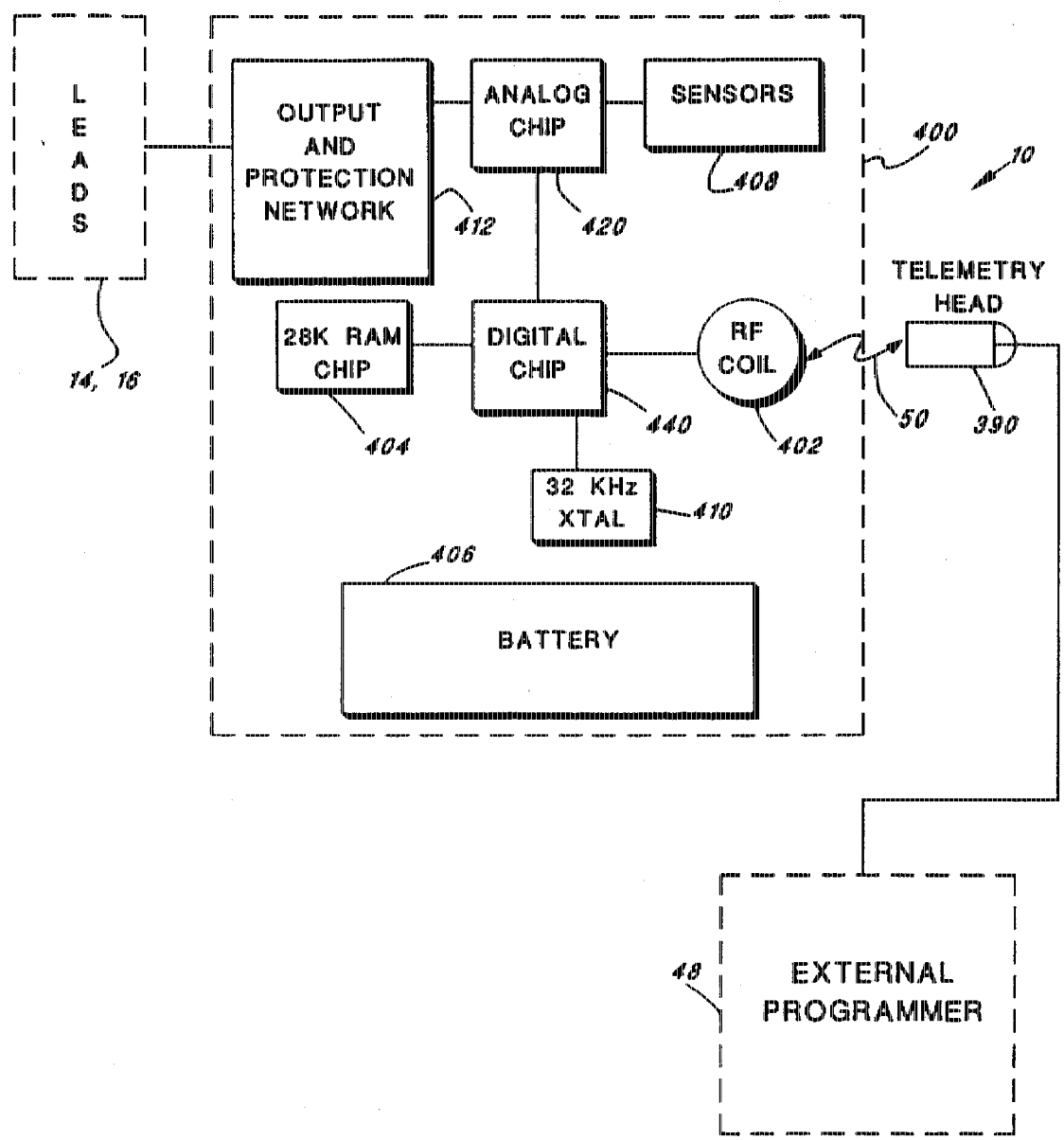
FIG. 6 is a block diagram that depicts, in accordance with one embodiment of the invention, the main hardware components of the implantable electronic pacemaker of FIG. 1.
Figure 7:
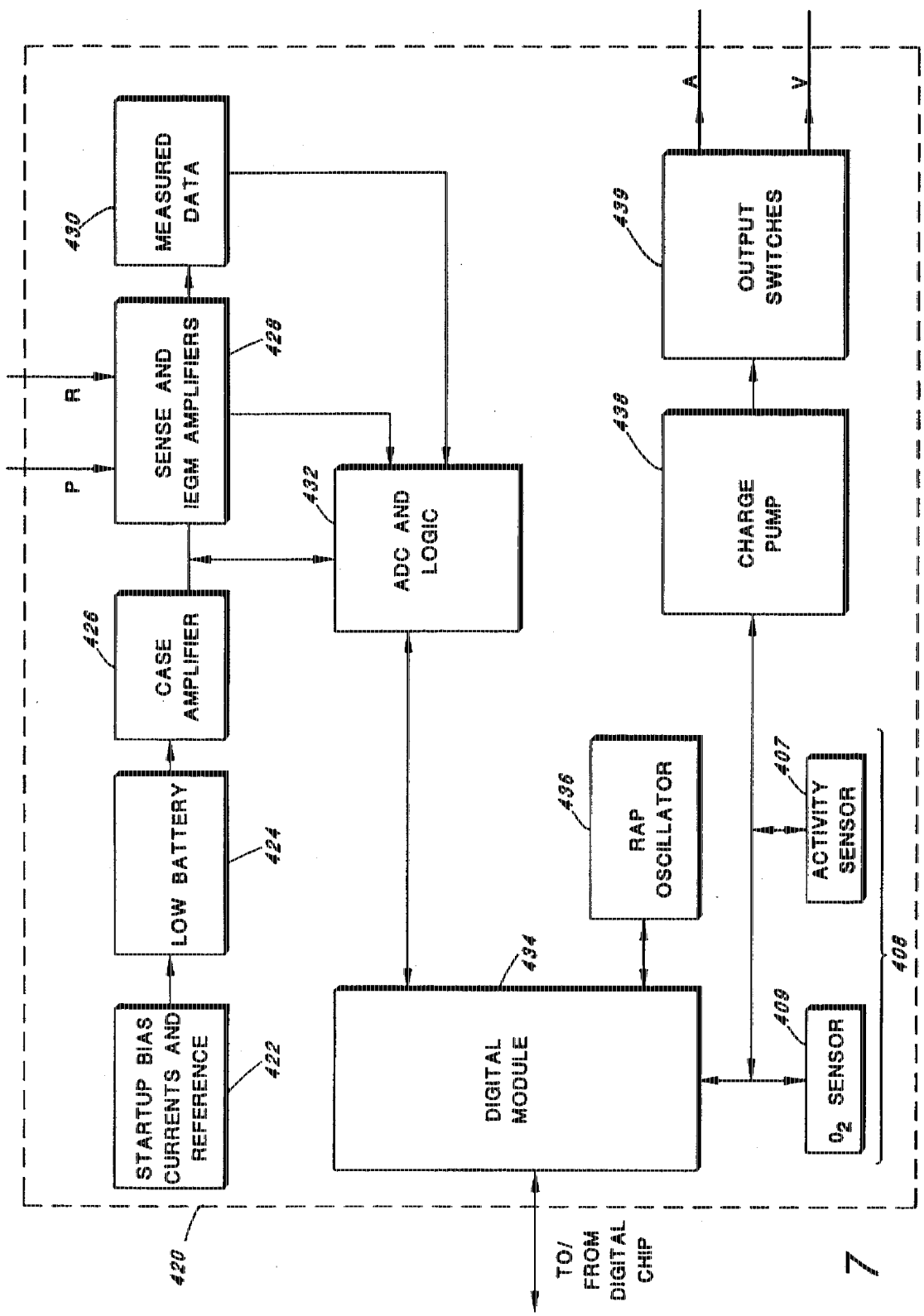
FIG. 7 is a block diagram of the analog chip portion of the electronic pacemaker of FIG. 6.
Figure 8:
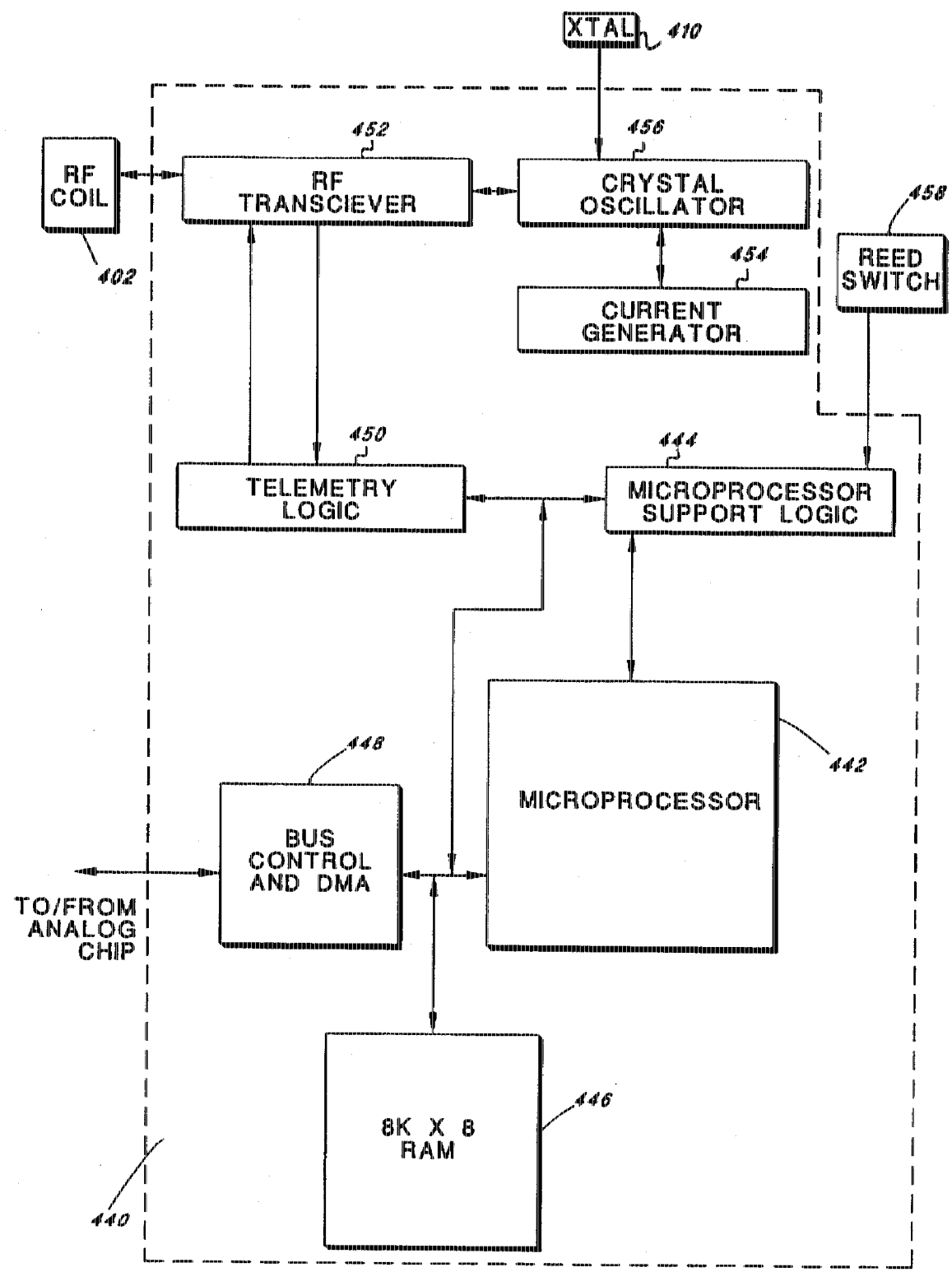
FIG. 8 is a block diagram of the digital chip portion of the electronic pacemaker of FIG. 6, and illustrates the use of a microprocessor controlled to traverse the steps illustrated in FIG. 5.

A control circuit or control system 26 controls the dual-chamber pacemaker 10. The control system 26 may be implemented using, e.g., discrete hardware components, a state machine-type design or, preferably, a microprocessor modified with a software routine to carry out the functions described herein. An exemplary implementation using a microprocessor-based design is shown in FIGS. 6, 7 and 8, below. In one embodiment, the microprocessor is modified with a software routine to carry out the steps shown in the flowchart of FIG. 5. An exemplary software routine can easily be generated by one skilled in the art to carry out the steps illustrated in FIG. 5. An alternative microprocessor-based design is shown in U.S. Pat. No. 4,940,053, incorporated herein by reference.

The control system 26 receives output signals from the atrial channel sense amplifier 22 over a signal line 28. Similarly, the control system 26 receives output signals from the ventricular channel sense amplifier 24 over a signal line 30. The output signals on the signal lines 28, 30 are generated each time a P-wave or an R-wave, respectively, is sensed within the heart 12 through the electrodes/leads 14, 15, 16 and 17.

The control system 26 also generates trigger signals that are sent to the atrial pulse generator 18 and the ventricular pulse generator 20 over respective signal lines 32, 34. These trigger signals are generated each time a stimulation pulse is to be generated by the respective pulse generator 18 or 20. The stimulation pulse generated by the atrial pulse generator 18 is referred to as an "A-pulse," and the stimulation pulse generated by the ventricular pulse generator 20 is referred to as a "V-pulse." During the time that either the A-pulse or V-pulse is being delivered to the heart, a corresponding amplifier, i.e., the P-AMP 22 or the R-AMP 24, is typically disabled by way of a blanking signal presented to the corresponding amplifier by the control system 26 over a respective signal line 36 or 38. This "blanking" action prevents the amplifiers from becoming saturated by the relatively large A-pulse or V-pulse, respectively, present at the input terminals of the corresponding amplifier 22 or 24.

Upon the generation of the stimulation pulse, the control system 26 initiates two time periods: an evoked response detection time period and a refractory time period. Both time periods start simultaneously, but the refractory time period is programmed to last longer than the evoked response detection time period. During the evoked response detection time period (referred to as the atrial evoked response detection window (AERDW) or the ventricular evoked response detection window (VERDW), depending on whether an A-pulse or V-pulse was generated), the appropriate amplifier 22 or 24 is enabled, and any cardiac activity detected during the AERDW or VERDW is presumed to be an evoked response. Extending beyond the expiration of the AERDW is the atrial refractory period (AREF) and extending beyond the expiration of the VERDW is the ventricular refractory period (VREF). During the portion of the refractory period (AREF or VREF) that extends beyond the evoked response detection time period (AERDW or VERDW), the amplifiers 22, 24 may again be disabled by the blanking signal so as to prevent the sensing of residual electrical signals that may be present on the leads 14, 16 following pacemaker stimulation, which electrical signals could falsely be interpreted as P-waves or R-waves. Thus, the blanking signal may be applied to the P-AMP 22 for a period of time following the AERDW, and may be applied to the R-AMP 24 for a period of time following the VERDW. Alternatively, and preferably, the sense amplifiers 22, 24 may remain enabled and the control system 26 may become insensitive to, or ignore, any cardiac activity detected during this portion of the atrial or ventricular refractory period.

The control system 26 of electronic pacemaker 10 detects whether capture has been achieved by determining whether an evoked P-wave or R-wave has occurred during the AERDW or VERDW, as explained more fully below in reference to FIG. 2. A variation of this capture-determining technique is further explained below in reference to FIG. 4.

Still referring to FIG. 1, the electronic pacemaker 10 also includes a memory circuit 40 that is coupled to the control system 26 over a suitable data/address bus 42. The memory circuit 40 allows certain control parameters, used by the control system 26 in controlling the operation of the electronic pacemaker 10, to be programmably stored and modified, as required, in order to customize the electronic pacemaker's operation to suit the needs of a particular patient. Such data includes the basic timing intervals used during operation of the pacemaker, such as an atrial escape interval (AEI), an atrioventricular interval (AVI), the atrial refractory period (AREF), the ventricular refractory period (VREF), the atrial evoked response detection window (AERDW), and the ventricular evoked response detection window (VERDW). Further, data sensed during the operation of the electronic pacemaker 10 may be stored in the memory 40 for later retrieval and analysis.

A telemetry circuit 44 is further included in the electronic pacemaker 10. This telemetry circuit 44 is connected to the control system 26 by way of a suitable command/data bus 46. In turn, the telemetry circuit 44, which is included within the implantable electronic pacemaker 10, may be selectively coupled to an external programming device 48 (or external programmer) by means of an appropriate communication link 50. The communication link 50 may be any suitable electromagnetic link, such as a radio frequency (RF) communications channel, an inductively-coupled link, an optical link, an infrared link, or the like. Advantageously, through the external programmer 48 and the communication link 50, desired commands and parameters may be sent to the control system 26. Similarly, through this communication link 50 and the external programmer 48, data (either held within the control system 26, as in a data latch, or stored within the memory 40), may be remotely (i.e., from outside the patient in which the electronic pacemaker 10 is implanted) received from the electronic pacemaker 10. In this manner, non-invasive communications can be established from time to time with the implanted electronic pacemaker 10 from a remote, non-implanted, location. Further details associated with the use of an external programmer that sends and receives data from an implanted pacemaker may be found in, e.g., U.S. Pat. No. 4,847,617, issued to Silvian, entitled "High Speed Digital Telemetry System for Implantable Devices," incorporated herein by reference.

The electronic pacemaker 10 in FIG. 1 is referred to as a dual-chamber pacemaker because it interfaces with both the atria and the ventricles of the heart. Those portions of the electronic pacemaker 10 that interface with the atria, e.g., the lead 14, the P-AMP 22, the atrial pulse generator 18, and corresponding portions of the control system 26, are commonly referred to as the atrial channel. Similarly, those portions of the electronic pacemaker 10 that interface with the ventricles, e.g., the lead 16, the R-AMP 24, the ventricular pulse generator 20, and corresponding portions of the control system 26, are commonly referred to as the ventricular channel.

In accordance with one embodiment of the present invention, the electronic pacemaker 10 may further include one or more sensors 52 that is/are connected to the control system 26 over a suitable connection line 54. Such sensor 52 is used to sense some physiological parameter that gives an indication of how fast, or how slowly, the patient's heart should be beating. Such information is then used by the pacemaker to control the pacing rate of the pacemaker so that the heart will be paced at the preferred rate. While the sensor 52 is illustrated in FIG. 1 as being included within the pacemaker 10, it will be understood by one skilled in the art that the sensor may also be external to the pacemaker 10, yet still be implanted within or carried by the patient. A common type of sensor is an activity sensor, such as a piezoelectric crystal, mounted to the case of the electronic pacemaker 10. Other types of sensors, such as physiologic sensors that sense the oxygen content of blood, respiration rate, pH of blood, and the like, may also be used in lieu of, or in addition to, the activity sensor. The type of sensor, if any, used is not critical to the present invention. Any sensor or combination of sensors capable of sensing body motion or a physiological parameter relatable to the rate at which the heart should be beating can be used. A pacemaker using such a sensor(s) is commonly referred to as a "rate-responsive" pacemaker because such a pacemaker adjusts the rate (i.e., atrial escape interval (AEI) and atrioventricular interval (AVI)) of the pacemaker in a manner that tracks the physiological needs of the patient.

Figure 2:
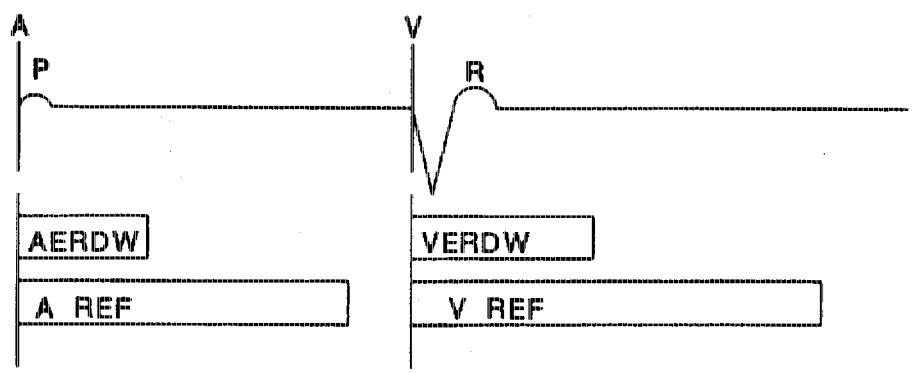
FIG. 2 is an illustration of an exemplary electrocardiographic signal, showing an evoked P-wave and R-wave in response to the implantable electronic pacemaker of FIG. 1 performing dual-chamber cardiac pacing, and further illustrates the timing windows or periods generated by the pacemaker in order to carry out the present invention.

Referring next to FIG. 2, an exemplary electrographic signal of an evoked P-wave and R-wave is shown in response to the generation of an A-pulse and V-pulse by the implantable electronic pacemaker 10 (FIG. 1). Also shown are the atrial evoked response detection window (AERDW), the atrial refractory period (AREF), the ventricular evoked response detection window (VERDW) and the ventricular refractory period (VREF). AS illustrated, the A-pulse (labeled "A" in FIG. 2) is generated by the atrial pulse generator 18, and the evoked P-wave occurs in response thereto. Thus, atrial capture is achieved. Also in response to the generation of the A-pulse, the atrial evoked response detection window (AERDW) and the atrial refractory period (AREF) are initiated. The AERDW typically ranges from 10–20 ms (or even as small as 100 µs) in duration, e.g., 15 ms, and the AREF typically ranges from 200–400 ms in duration, e.g., 300 ms, thus extending beyond the expiration of the AERDW. During the AERDW, any cardiac activity is detected through the lead 14. Any atrial activity sensed by the control system 26 is considered to be an atrial evoked response (evoked P-wave), as shown in FIG. 2. Following the AERDW, and before the expiration of the AREF, the control system 26 is insensitive to cardiac activity. Following the atrial refractory period, the control system 26 is again sensitive to cardiac activity, such as spontaneous atrial contractions, or intrinsic atrial activity.

At a specified time following delivery of the A-pulse, a ventricular stimulation pulse (V-pulse) is generated by the ventricular pulse generator 20, and, as shown in FIG. 2, a ventricular evoked response (evoked R-wave) occurs in response thereto. Thus, ventricular capture is achieved. Also in response to the generation of the V-pulse, the ventricular evoked response detection window (VERDW) and the ventricular refractory period (VREF) are initiated. The VERDW typically ranges from 10–50 ms (or even up to 150 ms), and the VREF typically ranges from 200 ms to 300 ms longer than the VERDW. During the VERDW, the control system 26 is sensitive to ventricular cardiac activity as detected through the lead 16, and specifically to the ventricular evoked response (R-wave) shown in FIG. 2. Following the VERDW, and before the expiration of the VREF, the control system 26 is insensitive to cardiac activity, which activity is assumed to be residual electrical signals resulting from the ventricular stimulation pulse (V-pulse) or from the evoked response (evoked R-wave). Following the ventricular refractory period, the control system 26 is again sensitive to cardiac activity, such as spontaneous ventricular contractions, or intrinsic ventricular activity.

Figure 3:
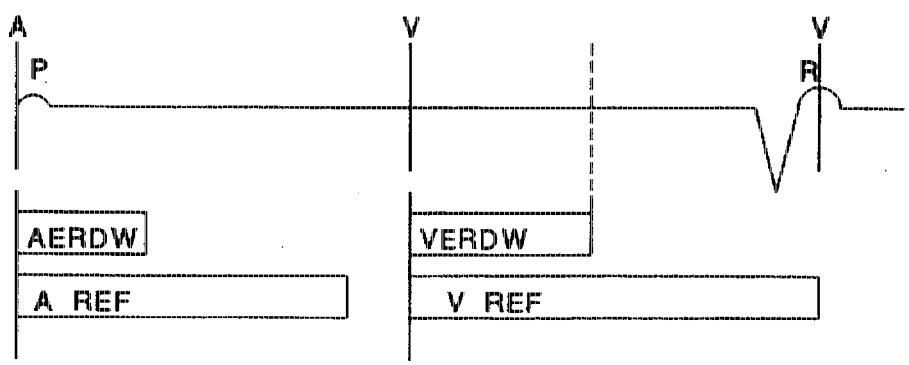
FIG. 3 is an exemplary electrographic signal as in FIG. 2 showing what might happen in response to an implantable electronic pacemaker operating in accordance with the teachings of the prior art.

Referring next to FIG. 3., an exemplary electrographic signal is shown as might occur in response to an implantable electronic pacemaker being operated in a conventional prior art manner. As in FIG. 2, an A-pulse is followed by an evoked P-wave, thus evidencing that atrial capture has been achieved. Unlike FIG. 2, however, the V-pulse does not achieve capture, so no evoked R-wave immediately follows the V-pulse. Instead, the ventricular evoked response detection window expires before any cardiac activity is sensed through the lead 16. As a result of VERDW expiring without an evoked R-wave having been sensed, and in accordance with an autocapture mode of operation, backup ventricular support is invoked, including the generation of a backup V-pulse shortly after the expiration of the VERDW. Unfortunately, as illustrated in FIG. 3, a spontaneous R-wave occurs during a period of insensitivity following the expiration of the VERDW, but before the expiration of the VREF, i.e., while the control system is electrically refractory and thus insensitive to cardiac activity. Because the control system is refractory, the spontaneous R-wave goes undetected and the backup V-pulse is generated approximately simultaneously with the undetected spontaneous R-wave. This causes energy to be wasted, and may be dangerous in that it can cause an arrhythmia to occur.

Figure 4:
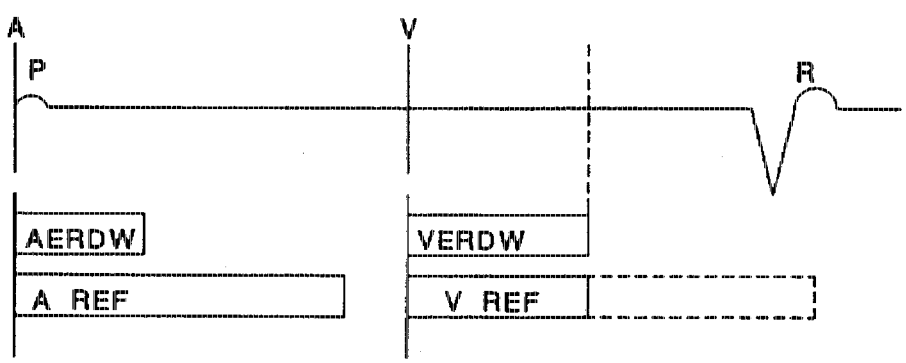
FIG. 4 is an exemplary electrographic signal as in FIG. 2 showing a desired response when the implantable electronic pacemaker operates in accordance with one embodiment of the present invention.

Referring to FIG. 4, an exemplary electrographic signal is shown as might occur in response to the implantable pacemaker operating in accordance with one embodiment of the present invention. In FIG. 4 (as in FIGS. 2 and 3), an A-pulse is followed by an evoked P-wave, thus evidencing that atrial capture has been achieved. Following the P-wave, a V-pulse is generated, which initiates the VERDW and VREF windows. As in FIG. 3, the V-pulse does not achieve capture so no evoked R-wave is detected before the expiration of the VERDW. Hence, backup ventricular support is initiated in accordance with an autocapture mode of operation. However, unlike known implantable electronic pacemaker systems, such as those that operate as illustrated in FIG. 3, the electronic pacemaker operating as illustrated in FIG. 4 terminates or cuts short the VREF whenever a determination is made that capture has not occurred, i.e., that an evoked R-wave did not occur. As shown in FIG. 4, the termination of VREF can occur simultaneously with the expiration of the VERDW. As a result of VREF being terminated (or cut short), the control system 26 remains sensitive following the VERDW, and the spontaneous R-wave that follows is therefore detected. Such detection immediately causes the backup ventricular support to terminate before a backup V-pulse is generated, thereby preventing the backup V-pulse from being applied during the spontaneous R-wave. In this manner, the present invention determines whether a backup electrical stimulation pulse can be safely delivered to the heart following delivery of an ineffective electrical stimulation pulse for which capture was not achieved, i.e., for which no evoked response was detected.

Figure 5:
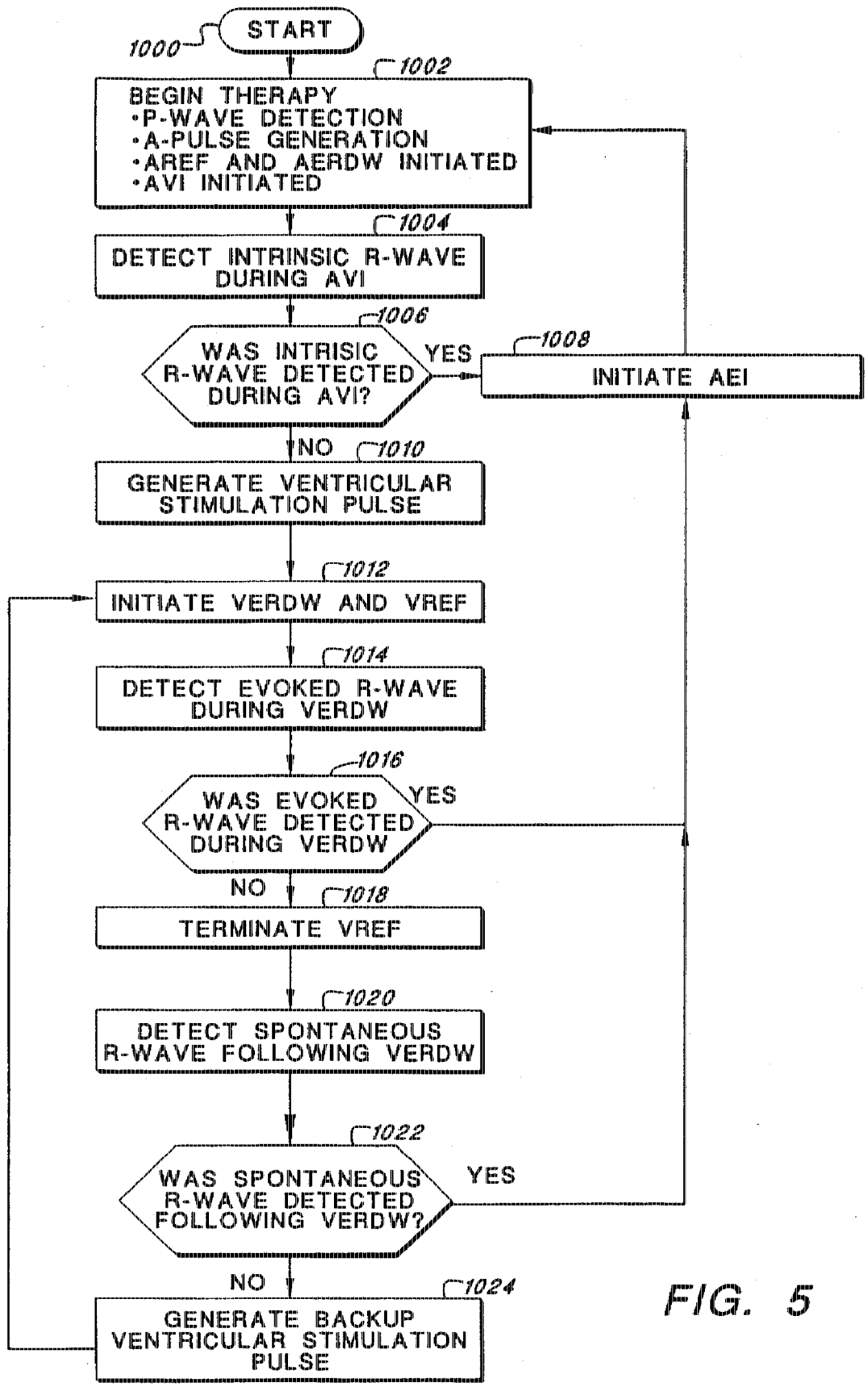
FIG. 5 is a flowchart showing the steps traversed by the electronic pacemaker of FIG. 1 when operating in accordance with one embodiment of the invention.

Turning next to FIG. 5, a flowchart is shown of the steps traversed by the electronic pacemaker 10 as it carries out one embodiment of the present invention. A software routine can be coded by one skilled in the art in order to effectuate the method of FIG. 5 within an off-the-shelf-type microprocessor or a microprocessor within an application specific integrated circuit (ASIC). Such microprocessor or ASIC can in turn be used to implement the control system 26, or equivalent control device. As shown in FIG. 5, as the pacemaker starts its programmed operation (Block 1000) the microprocessor is instructed to provide cardiac therapy, including, e.g., P-wave detection, A-pulse generation, and initiation of an AV interval (AVI). The particular type of cardiac therapy applied will vary depending upon the particular pacing modality used to carry out the teachings of the present invention. As described herein, the present embodiment is carried out using an electronic pacemaker operating in a DDD modality. After providing such therapy, the microprocessor next detects (1004) whether an intrinsic R-wave occurs following an intrinsic P-wave (or, following an atrial stimulation pulse (A-pulse)) during the AVI. In the event an intrinsic R-wave is detected (Block 1006), an atrial escape interval (AEI) is initiated (Block 1008) and the appropriate cardiac therapy is again initiated (Block 1002). Execution continues (Blocks 1004 et seq.), as described above. In the event, however, an intrinsic R-wave is not detected during the AVI (Block 1006), a ventricular stimulation pulse is generated (Block 1010) and a ventricular evoked response detection window (VERDW) and ventricular refractory period (VREF) are initiated (Block 1012).

Next, the electronic pacemaker detects (1014) whether an evoked R-wave occurs during the VERDW. Such detection is achieved by sensing whether any ventricular cardiac activity is present during the VERDW. In the event an evoked R-wave is detected during the VERDW (Block 1016) the atrial escape interval is again initiated (Block 1008), and the appropriate therapy is again started (Block 1002) and the process continues (Blocks 1004 et seq.), as described above. In the event, however, an evoked R-wave is not detected during the VERDW (Block 1016), the ventricular refractory period is immediately terminated or cut short (Block 1018). Such action renders the electronic pacemaker sensitive to ventricular cardiac activity, so that the electronic pacemaker is able to detect (Block 1020) whether a spontaneous R-wave occurs following the VERDW. If a spontaneous R-wave is detected during VERDW (YES branch of Block 1022), then the atrial escape interval is initiated (Block 1008), and the process repeats (Blocks 1002 et seq.) as described above. However, in the event a spontaneous R-wave is not detected following VERDW (NO branch of Block 1022), a backup ventricular stimulation pulse may be generated (Block 1024), and the VERDW and VREF periods are again initiated (Block 1012). In this way, a backup ventricular stimulation pulse is prevented from being generated when a primary (or initial) ventricular stimulation pulse fails to achieve capture, thereby eliminating the possibility that such backup pulse might be generated and delivered into a spontaneous R-wave that occurs after the VERDW.

Referring next to FIG. 6, there is shown a preferred configuration of a pacing system that implements the functions described in connection with FIG. 1. The system includes the external programmer 48, the electronic pacemaker 10, and the leads 14, 16. The leads 14, 16 include conventional atrial and ventricular leads 14, 16 and electrodes 15, 17, as described previously. Additional leads may also be employed such as an oxygen sensor lead (not shown), which lead contains an LED-detector assembly used to measure the oxygen content of the blood. Such a lead is described, e.g., in U.S. Pat. No. 4,815,469, incorporated herein by reference.

The external programmer 48 includes a telemetry head 390 that is positioned proximate the implantable pacemaker 10 whenever the communication link 50 is to be established between the electronic pacemaker 10 and the external programmer 48. The external programmer 48 may be of conventional design, as described, e.g., in U.S. Pat. No. 4,809,697, incorporated herein by reference.

The components of the electronic pacemaker 10 are housed within a hermetically sealed case or housing 400 (which case or housing is represented in FIG. 6 by the dashed line 400). The case 400 is preferably a titanium metal case. The components within the case 400 include an RF coil 402, a memory chip 404, a battery 406, one or more sensors in a sensor circuit 408, a crystal 410, an output/protection network 412, an analog chip 420 and a digital chip 440.

The battery 406, which is by volume the largest component within the pacemaker 10, may be of conventional design, and is a lithium battery that provides operating power to all of the electronic circuits within the pacemaker. The RF coil 402 is used to establish the communication link 50 with the telemetry head 390. The crystal 410 is used in conjunction with a crystal oscillator circuit on the digital chip 440 (described below) to provide a stable frequency clock signal. In the preferred embodiment, the frequency of the crystal oscillator is 32 KHz, although any suitable frequency could be used. The sensor circuit 408 includes appropriate sensors used by the pacemaker as it carries out rate-responsive pacing functions. For example, in one embodiment, the sensor circuit 408 includes an accelerometer adapted to sense patient activity.

The memory chip 404 is a low-power static random access memory (RAM) chip wherein the operating parameters, e.g., control variables, of the pacemaker 10 may be stored, and wherein sensed data may be stored, as required. The analog chip 420 and the digital chip 440 contain electronic circuits that perform processing and control functions of the pacemaker 10. The analog and digital chips 420, 440 are advantageously designed to minimize the number of components needed external thereto for operation of the pacemaker 10. The analog chip 420 interfaces with the leads 14, 16 through the output and protection network 412, which network includes output capacitors, appropriate feed-through connectors to allow electrical connection through the hermetically sealed case 400, and the like, as are commonly used in implantable medical devices.

Referring next to FIG. 7, a block diagram of the analog chip 420 is shown. The analog chip 420 contains all necessary sub-systems and modules to interface to the leads 14, 16 and the digital chip 440. For example, a startup/bias-current/reference module 422 generates the power-up signals used to initialize the pacemaker 10 when battery power is first applied. A low battery module 424 detects four voltage levels of the battery voltage for determining the battery status. A case amplifier 426 generates a case bias voltage that is used as a reference for the sense and intracardiac electrogram (IEGM) amplifier module 428. The module 428 includes the P-wave amplifier 22 and the R-wave amplifier 24, described above in FIG. 1. A measured data module 430 measures the battery voltage and current and other analog parameters of the pacing system. An ADC and Logic module 432 includes an analog-to-digital converter (ADC) and timing logic used to convert the analog signals of the pacemaker into 8-bit digital words. These digital words are then passed to a digital module 434, which module is used to generate all the basic timing and bus control functions as data is passed back and forth between the analog chip 420 and the digital chip 440.

Still referring to FIG. 7, it is seen that a Runaway Protection (RAP) circuit oscillator 436 is also coupled to the Digital Module 434. Such oscillator 436 provides an independent time base for limiting the highest pacing rate allowed by the pacemaker. Further coupled to the digital module 434 is the sensor network 408. The sensor network 408 includes appropriate sensors for sensing activity and other parameters. For example, an oxygen ($O_2$) sensor circuit 409 may be used in conjunction with the oxygen sensor lead, when used, to measure blood oxygen of the patient in which the electronic pacemaker 10 is implanted. An activity sensor 408 may also be used to sense patient activity as measured, e.g., by an accelerometer. A charge pump circuit 438 generates the output voltages for the stimulation pulses that are delivered to the patient's heart. A network of output switches 439 connects the charge developed by the pump circuit 438 to the leads 14, 16 at appropriate times to form appropriate stimulation pulses.

It is thus seen that the analog chip 420 contains the necessary circuitry to sense and detect atrial or ventricular events, digitize IEGM waveforms, measured data and other various analog signals, and provide such sensed and digitized signals to the digital module 434 for use by the digital chip 440. The charge pump circuit 438 acts as a voltage doubler/tripler for high output pulse capability. The output pulse width is controlled by the output switches 439. The condition of the battery is monitored, and independent Runaway Protection is provided.

Turning next to FIG. 8, it is seen that the main control element of the electronic pacemaker 10 is a microprocessor 442, which microprocessor is included within the digital chip 440. The microprocessor is modified with a software routine to carry out the steps described in FIG. 5, or in accordance with another desired control method. The digital chip 440 contains all the necessary logic to interface the analog chip 420 with the internal microprocessor 442. The microprocessor 442 includes a basic central processing unit (CPU) and 8 kilobytes (K) of static RAM. In addition, an 8K by 8K RAM 446 is connected to the microprocessor 442 to store data and programs. Microprocessor support logic 444, also coupled to the microprocessor 442, includes interrupt logic, timer logic, noise/sensed event logic, and magnet status logic. A bus controller 448 is further included on the digital chip 440 to provide direct memory access (DMA) timing and control of data transfer with the analog chip 420, including timing and control of the analog-to-digital converter 432 (FIG. 7) and telemetry communications. Telemetry channel logic 450 contains clock logic, IEGM and marker logic, telemetry command protocol logic, telemetry interrupt logic, error checking logic and CPU reset logic. An RF transceiver 452, coupled to the RF coil 402, transmits and receives telemetered data to and from the external programmer 48 through the telemetry head 390 (see FIG. 6). A crystal oscillator circuit 456, in conjunction with the crystal 410 (external to the digital chip 440), provides timing signals for pacemaker 10. A current generator 454 provides the bias currents for the digital chip. A reed switch circuit 458 detects the presence of a magnetic field, which magnetic field is present whenever the telemetry head 390 is in place on the patient's skin above the location where the pacemaker 10 is implanted.

The pacemaker 10 described above in connection with FIGS. 6-8 above provides the basic functions of the pacemaker described in connection with FIG. 1, plus other pacing/sensing functions as are known in the art. For purposes of the present invention, the pacemaker circuitry of FIGS. 6-8 sets the basic timing of the pacing interval, including setting an AV interval, and an atrial escape interval. The circuitry also provides for sensing or detecting natural ventricular events (R-waves) and/or natural atrial events (P-waves). This circuitry also initiates and generates the atrial and/or ventricular evoked response detection windows (AERDW and VERDW, respectively), and the atrial and ventricular refractory periods (AREF and VREF, respectively), described above and illustrated in FIGS. 2 and 4. Moreover, this circuitry includes the logic circuitry needed to terminate, or cut short, the VREF (or the AREF) period immediately upon determining that a given V-pulse (or A-pulse) has failed to achieve capture. Such failure to achieve capture is manifest, e.g., by the lack of an evoked R-wave (or any other ventricular activity) during the VERDW. It is to be understood, however, that other capture-determining techniques may also be used by the invention to signal that VREF (or AREF) may be cut short. That is, once a determination has been made that capture has not been achieved (using whatever capture-determining techniques are available), the present invention immediately terminates (cuts short) VREF (or AREF) because without capture, such intervals or periods are no longer needed. In particular, it is contemplated that in many instances, a determination can be made as to whether an evoked response has occurred before the expiration of the VERDW (or AERDW), in which case the VREF (or AREF) can immediately be terminated without waiting for the expiration of the VERDW (or AERDW).

While the invention herein disclosed has been described by means of specific embodiments and applications thereof, numerous modifications and variations could be made thereto by those skilled in the art without departing from the scope of the invention set forth in the claims.

What is claimed is:

1. In an implantable electronic pacemaker, a method of controlling when a backup stimulation pulse is generated and delivered to a patient's heart, the method comprising:

generating a first cardiac stimulation pulse;

initiating an evoked response detection time period in response to the generation of the first cardiac stimulation pulse;

initiating a refractory time period in response to the generation of the first cardiac stimulation pulse, the refractory time period being a longer time period than the evoked response detection time period;

detecting whether an evoked response occurs during the evoked response detection time period; and terminating the refractory time period in the event an evoked response did not occur during the evoked response detection time period;

detecting whether a spontaneous response occurs following the terminating of the refractory time period; and generating a backup cardiac stimulation pulse only when a spontaneous response does not occur following the terminating of the refractory time period.

2. The method of claim 1, wherein the evoked response detection time period is at least 100 microseconds and no more than 150 milliseconds.

3. The method of claim 2, wherein the evoked response detection time period is less than 20 ms.

4. The method of claim 1, wherein the step of generating the first cardiac stimulation pulse comprises generating a ventricular stimulation pulse.

5. The method of claim 1, wherein the step of generating the first cardiac stimulation pulse comprises generating an atrial stimulation pulse.

6. The method of claim 1, wherein the step of terminating the refractory time period comprises terminating the refractory time period simultaneously with the expiration of the evoked response detection time period.

7. The method of claim 1, wherein the step of detecting whether an evoked response occurs during said evoked response detection time period comprises detecting whether an evoked response occurs before the expiration of the evoked response detection time period.

8. The method of claim 1, wherein the step of generating the backup cardiac stimulation pulse includes generating a second cardiac stimulation pulse of greater energy than the first cardiac stimulation pulse.

9. The method of claim 1, wherein the step of generating the backup cardiac stimulation pulse includes generating a second cardiac stimulation pulse of greater pulse width than the first cardiac stimulation pulse.

10. A method of operating an implantable pacemaker so as to enhance its ability to detect a natural cardiac contraction, said pacemaker having means for generating a cardiac stimulation pulse, means for defining a refractory period immediately following the stimulation pulse, means for detecting capture, and means for detecting natural cardiac contractions, said method comprising the steps of:

(a) issuing a cardiac stimulation pulse;

(b) determining if the issued cardiac stimulation pulse has achieved capture;

(c) terminating a refractory period of the pacemaker immediately upon determining that capture was not achieved; and (d) determining if a natural cardiac contraction occurs thereafter.

11. The method of claim 10, wherein step (a) comprises issuing a ventricular stimulation pulse and step (c) comprises terminating a ventricular refractory period as soon as a determination is made in step (b) that capture has not been achieved.

12. The method of claim 10, wherein step (a) comprises issuing an atrial stimulation pulse and step (c) comprises terminating an atrial refractory period as soon as a determination is made in step (b) that capture has not been achieved.

13. A method of operating an implantable pacemaker so as to enhance its ability to detect natural cardiac activity, said method comprising the steps of:

(a) generating a cardiac stimulation pulse;

(b) defining a refractory period during which cardiac activity is not sensed, said refractory period beginning when the cardiac stimulation pulse is generated, and terminating a prescribed number of milliseconds thereafter;

(c) detecting if a cardiac response is evoked by the cardiac stimulation pulse; and (d) cutting short the refractory period in the event no cardiac response is evoked by the cardiac stimulation pulse, thereby permitting cardiac activity to again be sensed.

14. The method of claim 13, wherein step (c) comprises:

defining an evoked response detection window that begins concurrent with the beginning of the refractory period; and determining if a cardiac response occurs during the evoked response detection window.

15. The method of claim 14, wherein step (d) comprises ending the refractory period coincident with the expiration of the evoked response detection window.

16. The method of claim 13, wherein step (d) comprises ending the refractory period immediately upon determining that no cardiac response is evoked by the cardiac stimulation pulse.

17. An implantable pacemaker comprising:

means for sensing cardiac activity;

means for generating a cardiac stimulation pulse;

timing means for defining a refractory period during which cardiac activity is not sensed;

detecting means for detecting if cardiac activity is evoked by the cardiac stimulation pulse; and terminating means for cutting short the refractory period in the event no cardiac response is evoked by the cardiac stimulation pulse, wherein cutting short the refractory period permits sensing of cardiac activity.

18. The implantable pacemaker, as set forth in claim 17, wherein the detecting means comprises:

means for defining an evoked response detection window that commences as soon as the cardiac stimulation pulse is generated; and means for sensing if a cardiac response occurs during the evoked response detection window.

19. The implantable pacemaker, as set forth in claim 18, wherein the terminating means comprises means for ending the refractory period coincident with the expiration of the evoked response detection window.

20. An implantable electronic pacemaker comprising:

pulse generator means for generating a first cardiac stimulating pulse;

first timing means for initiating an evoked response detection time period, the first timing means being coupled to the pulse generator means;

second timing means for initiating a refractory time period in response to the generation of the first cardiac stimulation pulse, the second timing means being coupled to the pulse generator means;

detecting means for detecting whether an evoked response occurs during the evoked response detection time period, the detecting means being coupled to the first timing means, the detecting means detecting whether a spontaneous response occurs following the terminating of the refractory time period; and terminating means for terminating the refractory time period in the event the detecting means detects that no evoked response occurs during the evoked response detection time period, the terminating means being coupled to the detecting means, the second timing means, and the pulse generator means;

the pulse generating means generating a second cardiac stimulation pulse in the event the detecting means detects that a spontaneous response did not occur following the terminating of the refractory time period.

* * * * *